United States Patent
Kosierkiewicz (10) Patent No.: US 9,402,997 B1
(45) Date of Patent: Aug. 2, 2016

(54) SYSTEM AND METHOD FOR STIMULATING MEDICAL ELECTRODE WITH A MEASUREMENT CAPABILITY

(71) Applicant: Tomasz Andrzej Kosierkiewicz, Mount Vernon, IL (US)

(72) Inventor: Tomasz Andrzej Kosierkiewicz, Mount Vernon, IL (US)

( * ) Notice: Subject to any disclaimer, the term of this patent is extended or adjusted under 35 U.S.C. 154(b) by 0 days.

(21) Appl. No.: 14/214,023

(22) Filed: Mar. 14, 2014

Related U.S. Application Data (63) Continuation-in-part of application No. 14/019,114, filed on Sep. 5, 2013, which is a continuation-in-part of application No. 13/020,392, filed on Feb. 3, 2011, now Pat. No. 8,569,935, which is a continuation-in-part of application No. 12/835,972, filed on Jul. 14, 2010, now abandoned, which is a continuation-in-part of application No. 12/559,061, filed on Sep. 14, 2009, now abandoned.

(60) Provisional application No. 61/788,662, filed on Mar. 15, 2013, provisional application No. 61/819,574, filed on May 4, 2013, provisional application No. 61/347,963, filed on May 25, 2010, provisional application No. 61/788,575, filed on Mar. 15, 2013.

(51) Int. Cl.
*A61N 1/00* (2006.01)
*A61N 1/18* (2006.01)
*A61B 5/00* (2006.01)

(52) U.S. Cl.
CPC ... *A61N 1/18* (2013.01); *A61B 5/00* (2013.01); *A61B 2560/00* (2013.01); *A61B 2562/00* (2013.01); *A61B 2562/0209* (2013.01)

(58) Field of Classification Search
CPC ............. A61N 1/00; A61N 1/02; A61N 1/04; A61N 1/18; A61N 1/372; A61N 1/0529; A61N 1/0539; A61N 1/0551; A61B 2560/0468; A61B 2562/0209; A61B 5/0408; A61B 5/0448; A61B 5/0478; A61B 5/0492; A61B 5/053; A61B 5/0537; A61B 18/14; A61B 5/00

See application file for complete search history.

(56) References Cited

U.S. PATENT DOCUMENTS 6,319,241 B1 * 11/2001 King et al. .................... 604/502
2010/0286554 A1 * 11/2010 Davis ................. A61B 5/04001
                                                                    600/554
2013/0197357 A1 * 8/2013 Green et al. .................. 600/424

* cited by examiner

*Primary Examiner* — Theodore Stigell
*Assistant Examiner* — Elizabeth K So
(74) *Attorney, Agent, or Firm* — Jessica Smith; Loza & Loza, LLP (57) ABSTRACT

A peripheral nerve conduction diagnosis system that utilizes an electrostimulation device having dry elastomer electrodes and a distance measuring device that allow a user to move the electrostimulation device along the skin of a patient while in constant contact with the skin and measure the distance moved.

16 Claims, 5 Drawing Sheets

SYSTEM AND METHOD FOR STIMULATING MEDICAL ELECTRODE WITH A MEASUREMENT CAPABILITY

CROSS-REFERENCE TO RELATED PATENTS

The present U.S. Utility Patent Application claims priority as a continuation-in-part of application Ser. No. 14/019,114, filed Sep. 5, 2013, which claims priority to both U.S. Provisional Application Ser. No. 61/788,575, filed Mar. 15, 2013, and U.S. Provisional Application Ser. No. 61/819,574, filed May 4, 2014, and which is a continuation-in-part of application Ser. No. 13/020,392, filed Feb. 3, 2011, now U.S. Pat. No. 8,569,935, a CIP of U.S. Utility patent application Ser. No. 12/835,972 having a filing date of Jul. 14, 2010 now abandoned, which is a continuation-in-part of application Ser. No. 12/559,061, filed Sep. 14, 2009, now abandoned, which claims benefit to U.S. Provisional Application Ser. No. 61/347,963, filed May 25, 2010, all of which are incorporated by reference herein and made part of the present U.S. Utility Patent Application for all purposes.

This present U.S. Patent Application claims priority to U.S. Provisional Application Ser. No. 61/788,662 filed Mar. 15, 2013, entitled "SYSTEM AND METHOD FOR A MEDICAL DRY ELECTRODE WITH A MEASUREMENT CAPABILITY", which is incorporated by reference herein and made part of the present U.S. Utility Patent Application for all purposes

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not applicable.

BACKGROUND OF THE INVENTION

1. Technical Field of the Invention

This invention relates generally to medical diagnostic equipment and in particular to systems and methods for performing peripheral neuromuscular diagnosis with the stimulating device utilizing dry electrodes and having distance measurement capability.

2. Description of Related Art

In the medical field, nerve conduction tests or procedures are used to assess the functional status of the peripheral neuromuscular system. In the use of nerve conduction tests, when a nerve is stimulated electrically a reactions occurs somewhere along the nerve. The reaction of the nerve to the stimulation can be monitored with recording electrodes strategically placed on the patient. Direct recording of the reaction can be made along sensory or mixed sensory nerves, while indirect recording of the reaction from a muscle can be used for motor conduction tests. Both orthodromic conduction (an impulse traveling in the normal direction in a nerve fiber) and antidromic conduction (an impulse traveling in the opposite direction to that of normal in a nerve fiber) can be studied because nerve stimulus propagation occurs proximally to and distally to the point of stimulation. The time relationship between the stimulus and the response can be displayed, measured and recorded.

In the evaluation of motor nerves, motor responses are recorded over the target muscle being studied. Typically a recording electrode is placed over the motor point of the target muscle. A physical location on the patient is chosen along the nerve supplying the target muscle, at a select distance from the recording electrode, whereby when the electrostimulation is applied at the location, the response to the muscle can be recorded. Similarly, for sensory nerves, responses are recorded over the target nerve using surface electrodes. At the constant distance, distal or peak latency can be measured.

Some of the nerves tested require distal and proximal stimulation (e.g. wrist, elbow, and arm for median nerve). In such a case, the distance between the stimulation sites has to be measured to calculate conduction velocities. The conduction velocity of a nerve is calculated by measuring the distance between two stimulation sites and dividing by the difference in latency from the more proximal stimulus site and the latency of the distal stimulus site. Traditionally this distance is measured with nothing more than a measuring tape.

Traditionally, electrodes on the simulator that are used to stimulate the nerves are made with steel or gold plated steel and require the use of a messy electrode gels as a conductive medium between the electrodes and the skin.

Accordingly, there is a need for systems and methods for providing more accurate distance measurements without the use of messy electrode gels.

DETAILED DESCRIPTION OF THE INVENTION

Figure 1:
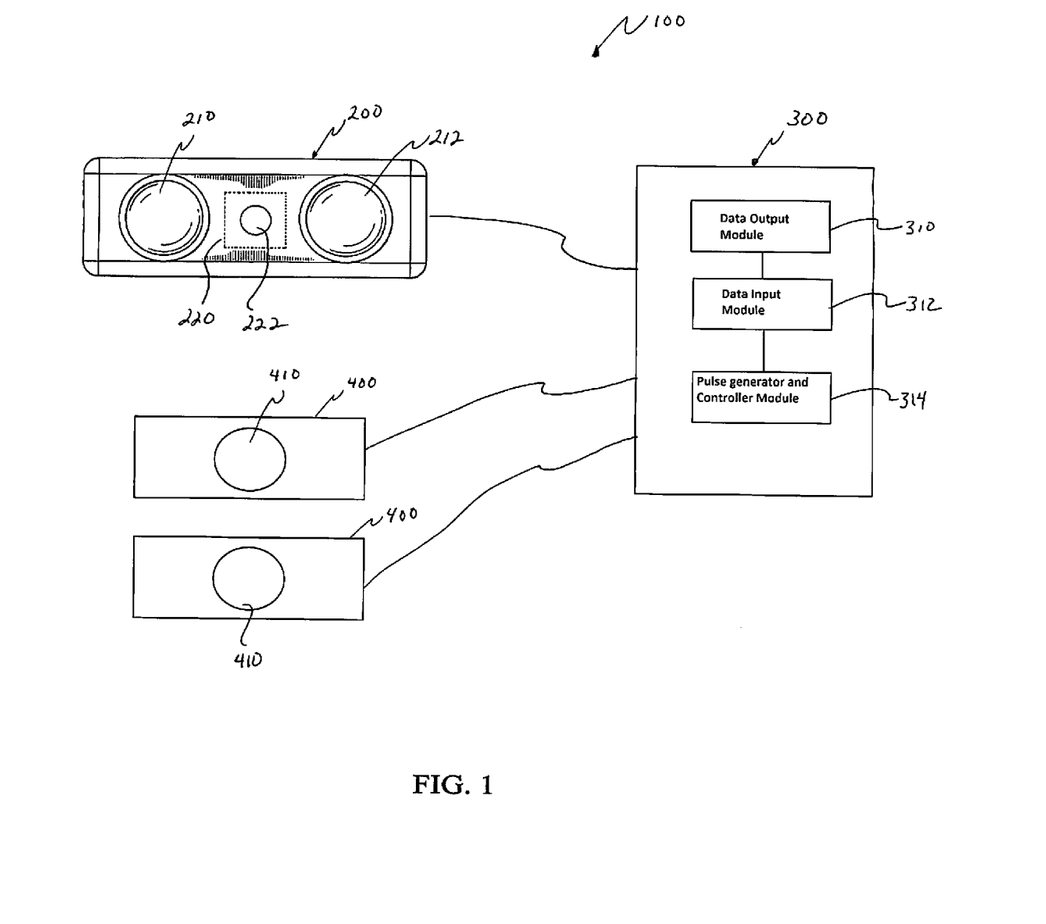
FIG. 1 illustrates diagram of an embodiment of a stimulation and diagnostic system.

FIG. 1 illustrates an embodiment of a stimulation and diagnostic system 100 for performing nerve conduction studies/diagnostics that includes an electrostimulation device 200, a programmable diagnostic device 300, and recording electrodes 400.

Electrostimulation device 200 is electrically connected to diagnostic device 300 and includes bar type stimulator probe with two dry electrodes, an active stimulating electrode (the cathode) 210 and an inactive stimulating electrode 212, and provides, via the dry electrodes, the output of an electrical stimulus received from the diagnostic device 300. Electrostimulation device 200 further includes a distance measurement module 220 to determine the distance electrostimulation device 200 is slid across the skin of the patient. Distance measurement module 220 includes a sensor 222 used to detect changes in distance the electrostimulation device 200 has been moved across a patient's skin between two specific user identified points.

Recording electrodes 400, which are electrically connected to diagnostic device 300, includes surface electrodes 410, and are used to monitor/detect/record the reaction of the targeted nerve or muscle to the applied stimulation from electrostimulation device 200. The type of recording electrodes 400 to be utilized is determined by the type of nerve response being diagnosed/studied, which may include by way of example, disc electrodes, ring electrodes and finger clip electrodes.

Although dry electrodes 210 and 212 are primarily used for stimulation and recording electrodes 400 are primarily used for monitoring/detecting/recording, it is contemplated that the any one of the electrodes could be used interchangeably for recording and stimulating.

Programmable diagnostic device 300, includes a data output module 310, such as a display screen, which outputs various information to the user regarding the operation of the diagnostic system 100. Programmable diagnostic device 300 also includes a data input module 312, such as various types of keyboards/keypads, data ports, data drives and the like, which facilitates the input of various types of information and programs from the electrodes and from user to operate programmable diagnostic device 300.

Programmable diagnostic device 300 also includes pulse generator and controller module 314, that among other things, controls operation of programmable diagnostic device 300, including the generation of the stimulation pulses sent to electrostimulation device 200, including pulse voltage and current, the pulse amplitude, frequency, duration and pulse width, as well as processing the data/information received from both electrostimulation device 200 and recording electrodes 400.

Figure 2:
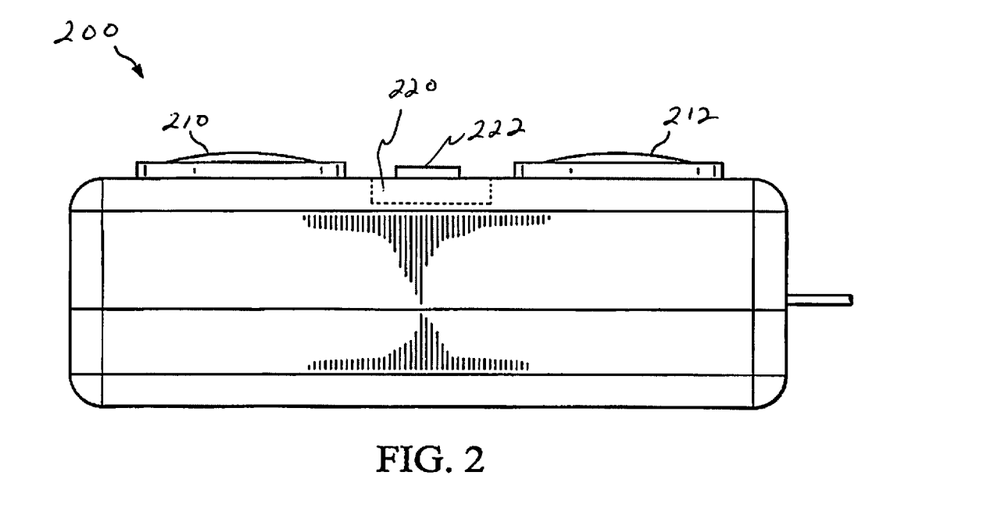
FIGS. 2 and 3 illustrate diagrams of an embodiment of a bar electrode with dry elastomer electrodes with a measurement module.
Figure 3:
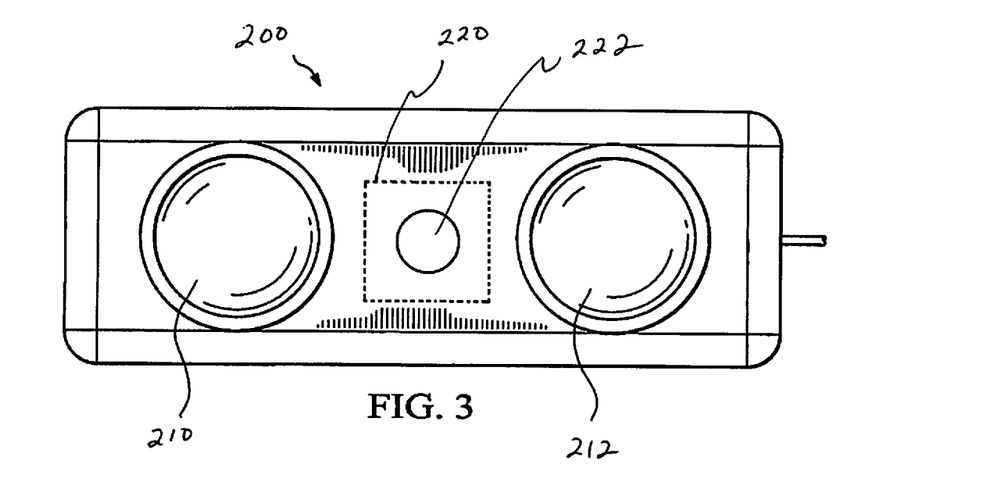

FIGS. 2 and 3 illustrate an embodiment of an electrostimulation device 200 including dry electrodes 210 and 212 with distance measurement module 220. In an embodiment, dry electrode 210 is configured as a cathode electrode and dry electrode 212 is configured as an anode electrode, although the polarities of the electrodes may be interchangeable between the two dry electrodes. As described above, electrostimulation device 200 is electrically connected to programmable diagnostic device 300 and receives electrical stimulation signals therefrom. When the dry electrodes 210 and 212 are in electrical contact with the skin of a patient, the received stimulation pulse traverses between the dry electrodes 210 and 212, through a portion of the patient, electrically stimulating a nerve of the patient proximate to the placement of the dry electrodes 210 and 212 thereon.

The electrostimulation device 200 includes a sensor 222, which, in an embodiment is positioned intermediate to electrodes 210 and 212, as part of the distance measurement module 220. In an embodiment, the distance measuring device comprises at least one distance measurement module 220. The distance measurement module 220 may include at least one light source drive, e.g., LED, infrared laser diode, or any other source of suitable form of electromagnetic radiation to cooperate with at least one photosensitive array incorporating a laser or other optical sensor 222 connected to a controller and to a digital signal processor (DSP) to determine a distance measurement as the electrostimulation device 200 is slid across the skin of a patient. For example, a distance measuring device is described in U.S. Pat. No. 5,194,906 issued on Mar. 16, 1993. U.S. Pat. No. 5,703,356 describes a sensor having an array of photosensitive elements which may be used in the measurement module herein. U.S. Pat. No. 7,656,508 describes another distance measuring apparatus that may be included in the measurement module herein. Other types of measuring techniques or devices may also be used herein. (It is noted, that the above cited patents are each incorporated herein by reference).

Alternatively, a smaller housing unit electrostimulation device 200 can be equipped with at least one optical fiber segment providing illumination to the aperture within the distance measurement module 220 of the electrostimulation device 200 from the at least one remote illumination source drive connected via the fiber optic cable (or cables) to the diagnostic device 300. Another fiber optic cable (or cables) connected to the at least one remote photosensitive array located within the sensing unit of the diagnostic device 300 would sense the reflected light through an aperture of the measurement module 220. (See by way of example, the optical mouse described in United States Patent Application No. 2007/0002020, which is incorporated herein by reference).

In operation, it is contemplated that the measured distance determined by distance measurement module 220 could be displayed in real time on the data output module 310 by programmable diagnostic device 300, and in yet another embodiment, a predetermined desired distance of movement could be programmed into programmable diagnostic device 300 for a specific procedure, such that, an audible or visual signal could be generated by programmable diagnostic device 300 on data output module 310 or the top surface of the electrostimulation device 200 housing, when the predetermined distance of movement of electrostimulation device 200 along the skin of the patient has been achieved by the operator.

In an embodiment—initially, to measure the distance between the active recording electrode 410 and the distal (first) stimulation site—the electrostimulation device 200 is positioned over the recording electrode 410 in a way that the stimulating electrode 210 is aligned with the active recording electrode 410. Stimulator 314 is activated by the user with a preset minimal current/voltage value thus activating the sensor module 222 to begin the measurement. The electrostimulation device 200 is then slid over to the presumed nerve position proximally at the distal (first) stimulation site (not shown). Once required distance value is met (e.g., 8 cm for medial nerve motor conduction) an audible or visible (e.g., red/green diode, such as on the top of electrostimulation device 200) signal will indicate it. Then, and only then, the stimulator 314 will unlock allowing the user to adjust the voltage/current settings to the required value for the supramaximal stimulation. Any departure from this position will cancel the measurement requiring it to start again from the initial step.

Now at the distal (first) stimulation site the supramaximal stimulating signal would set the beginning of the measurement and, provided the electrostimulation device 200 is slid from the distal (first) to the proximal (second) stimulation site in continuous contact with the skin, the second supramaximal stimulating signal (at the proximal stimulation site) will set the end of the measurement for the first segment, at this point the numeric data will be entered into an appropriate box in a table (not shown) and a display cursor will jump to the next position in the same table. At the same time the second stimulating signal would set the beginning of the measurement for the next, more proximal segment. The process can be repeated as needed.

In another embodiment, initially, to measure the distance between the active recording electrode 410 and the distal (first) stimulation site—the electrostimulation device 200 is positioned over the active recording electrode 410 in a way that the active stimulating electrode 210 is aligned and comes in contact with the active recording electrode 410. Stimulator 314 is activated by the user with a preset minimal current/voltage value thus activating the sensor module 222 to begin the measurement. At the same time the same current activates the circuitry of the recording electrodes 400 that otherwise would have been not connected to the circuitry (diagnostic device 300). Applying the current or the reference recording electrode 410 would not activate the circuitry for the recording electrodes 410

The electrostimulation device 200 is then slid over to the presumed nerve position proximally at the distal (first) stimulation site. Once a required distance value is met (e.g., 8 cm for medial nerve motor conduction), an audible or visible (such as a red/green diode on the top of electrostimulation device 200) signal will indicate it. Then, and only then, the stimulator 314 will unlock allowing the user to adjust the voltage current to the required value for the supramaximal stimulus. Any departure from this position will cancel the measurement requiring it to start again from the initial step.

Now at the distal (first) stimulation site the supramaximal stimulating signal would set the beginning of the measurement and, provided the electrostimulation device 200 is slid from the first to the proximal (second) stimulation site in continuous contact with the skin, the second supramaximal stimulating signal (at the proximal stimulation site) will set the end of the measurement for the first segment, at this point the numeric data would be entered into the appropriate box in a table (not shown) and the cursor will jump to the next position in the same table. At the same time the second stimulating signal will set the beginning of the measurement for the next, more proximal segment. The process can be repeated as needed.

As an exception, for the ulnar nerve, the wrist (W) to the above elbow (AE) segment would be a sum of the wrist (W) to the below elbow (BE) segment and the below elbow (BE) to the above elbow (AE) segments (not shown).

Though FIG. 3 illustrates a bar-type electrode, other types of electrodes or shapes or form factors may include the measurement module as well.

Figure 4:
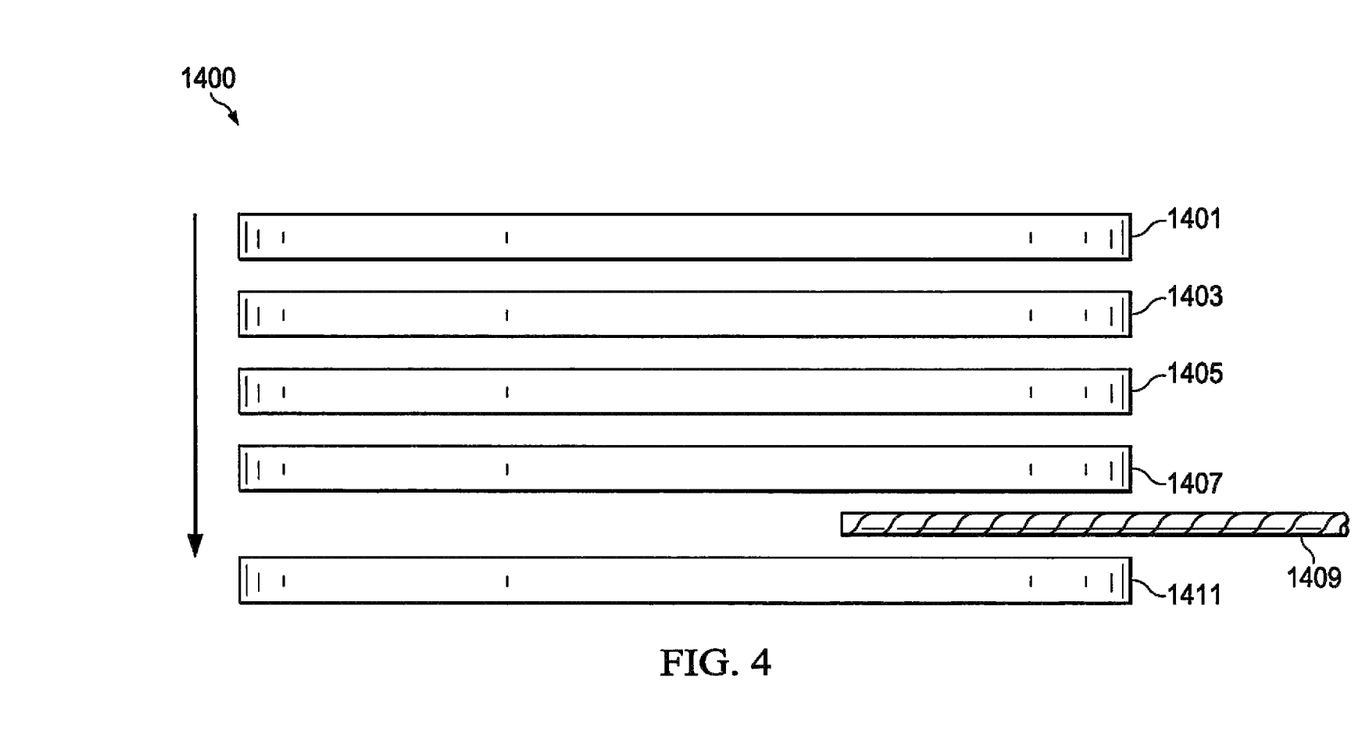
FIGS. 4, 5, 6 and 7 illustrate diagrams of various embodiments of dry elastomer electrodes.
Figure 5:
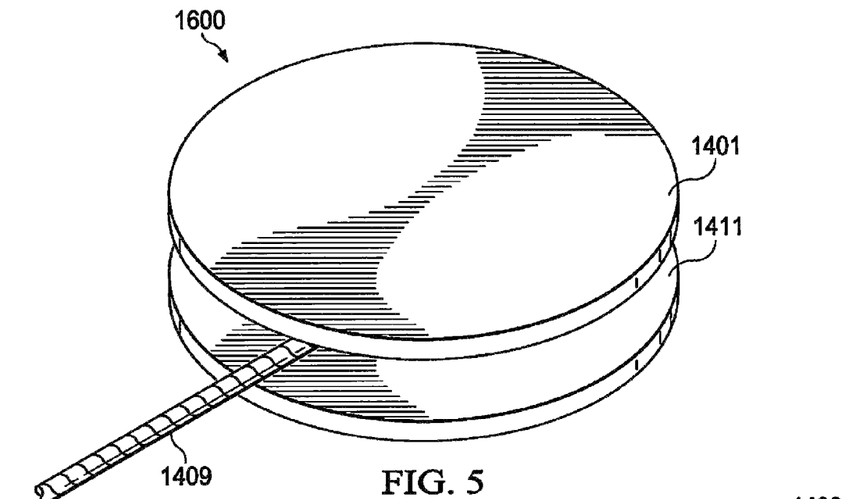
Figure 6:
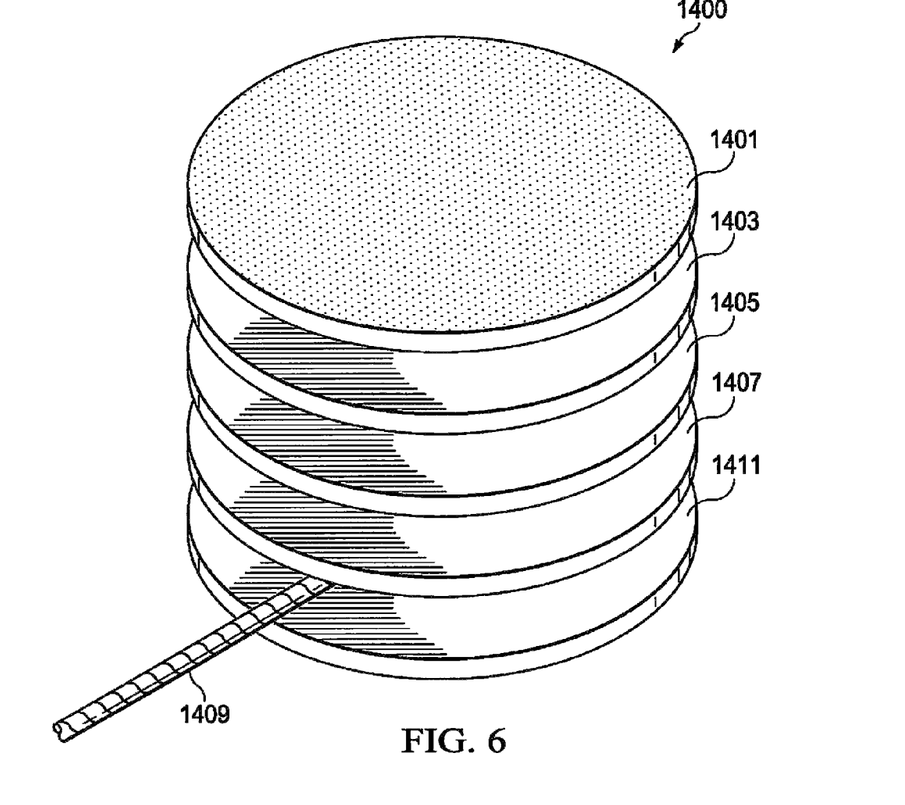

FIGS. 4-7 illustrate embodiments of a dry elastomer electrode utilized in the present invention, such as for dry electrodes 210 and 212 of electrostimulation device 200. Referring to FIGS. 4, 5 and 6, the electrodes 1400 and 1600 may be a transcutaneous medical electrode for stimulating nerves and/or muscles by generating electricity that could be used in different parts of the body. The electrodes 1400 and 1600 may be employed for other uses as well. In an embodiment, the electrodes 1400 and 1600 include a substantially dry body comfortable, electrically conductive interfacing layer of a metal-integral conductive silicon rubber sheet. The dry elastomer electrodes 1400 and 1600 are employed for similar uses as adhesive electrodes or gel electrodes or where such electrodes may not be appropriate or desirable. For example, the electrodes 1400 and 1600 may replace an adhesive electrode, e.g. where allergic reaction may be possible.

FIGS. 4 and 6 illustrate the electrode 1400 which includes in an embodiment at least an upper and first sheet 1401 of metal integral conductive silicon rubber (or elastomer) which, by way of example and not limitation, may be a gold, silver, silver plated copper, or other conductive metal plated material filled silicon. Electrode 1400 further includes a second layer 1403 which may be a conductive adhesive gel layer to adhere to the first sheet 1403, a third sheet 1405 of a conductive carbon film to adhere to the second layer 1403, a fourth sheet 1407 which may be a conductive metal sheet and the metal may be silver or other appropriate metals. An electrical lead 1409 is positioned and secured between the fourth sheet 1407 which may be conductive metal sheet and the metal may be silver or other appropriate metals. An electrical lead 1409 facilitates the delivery of energy to the electrode 1400 from a power source. Fifth sheet 1411 may be a dielectric/non-conducting flexible backing sheet.

FIG. 5 illustrates the electrode 1600 which includes two layers 1401 and 1411. Electrode 1600 includes an upper/first sheet 1401 of metal integral conductive silicon rubber (or elastomer) which, by way of example and not limitation, may be a silver, silver plated copper, or conductive metal plated material filled silicon. Electrode 1600 further includes an electrical lead 1409 which is positioned and secured between the first sheet 1401 and the bottom sheet 1411. The electrical lead 1409 facilitates the delivery of energy to the electrode 1600 from a power/recording source. The bottom sheet 1411 may be a dielectric/non-conducting flexible backing sheet.

Figure 7:
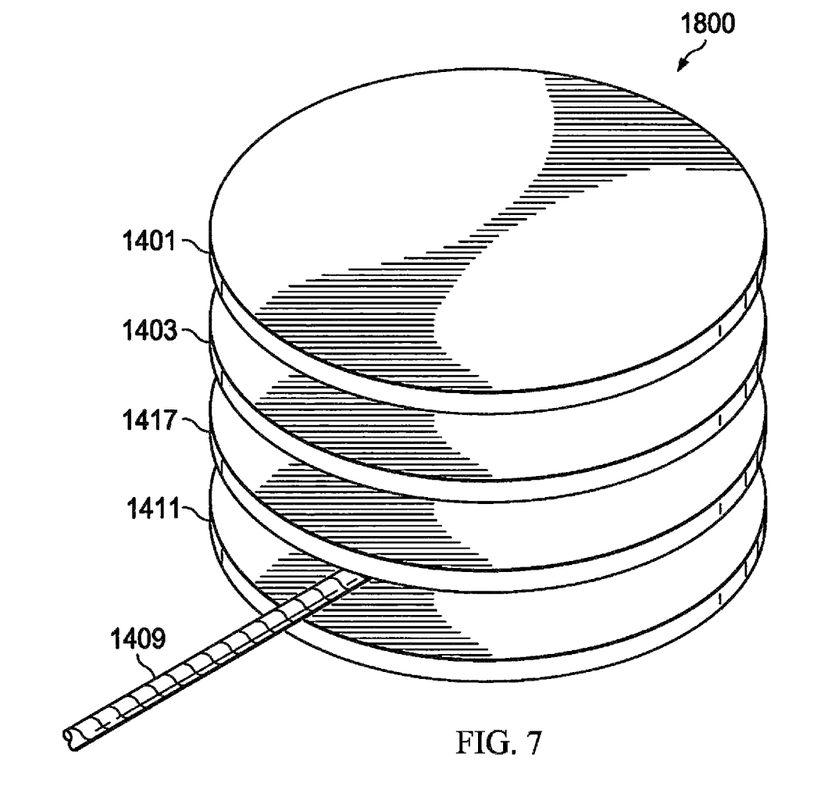

FIG. 7 illustrates another embodiment of an electrode 1800 which includes four layers 1401, 1403, 1417 and 1411. The first or top layer 1401 is the interfacing layer and is a silver filled silicon rubber (or elastomer) skin interface. The second layer 1403 is a conductive adhesive layer and is positioned in-between first layer 1401 and third layer 1417. The third layer 1417 is an Ag/AgCl film and is positioned between second layer 1403 and fourth layer 1411. The fourth layer 1411 is a dielectric backing layer and is positioned below third layer 1417. An electrical lead 1409 is positioned and secured between the third layer 1417 and the fourth layer 1411. The electrical lead 1409 facilitates the delivery of energy to the electrode 1800 from a power/recording source.

Though the interfacing or upper layer is described as including the metal integral conductive silicon rubber (or elastomer), other layers may also include the elastomer covering, e.g. conductive inks, or other materials, which may facilitate the prevention of corrosion. In addition, one or more other interfacing or upper layers may be added on top of the metal integral conductive silicon rubber (or elastomer) for interfacing with the skin. In another embodiment a plurality of metal integral conductive silicon rubber (or elastomer) layers may be used. The elastomer is preferably a conductive material with low volume resistivity, such as silver filled silicone rubber.

Though some embodiments of a dry elastomer electrode are shown in FIGS. 4-7, other types of dry electrodes may also be implemented in the various embodiments described herein.

With the use of dry electrodes in electrostimulation device 200, such as illustrated herein in FIGS. 4-7, and such as described in System and Method for Dry Elastomer Electrode, U.S. Provisional Application Serial No. 61/788,575, filed on Mar. 15, 2013, there is no need for any conductive gels to be placed between the electrodes and the skin of the patient, such that the dry electrode may cleanly slide across the skin and without the smearing of any conductive gels. In an embodiment, a dry bar electrode has a measurement module capable of measuring a distance as the dry bar electrode is slid across the skin.

By way of example of operation of an embodiment of stimulation and diagnostic system 100 of the present invention, the dry electrodes 210 and 212 of electrostimulation device 200 can be used in testing for ulnar neuropathy at the elbow. The proper number of recording electrodes 400 are attached at the specific targets on the patient. At a first stimulation site, upon activation, a first stimulation set is generated by the programmable diagnostic device 300 and delivered to the patient via electrodes 210 and 212. The corresponding reactions are recorded by the recording electrodes 400 and sent to the programmable diagnostic device 300. At the same time the measuring module 220 of the electrostimulation 200 device is activated. The electrostimulation device 200 is then slid from the first stimulation position to the second stimulation position with electrodes 210 and 212 in constant contact with the skin of the patient, during which measurement module 220 calculates the traversed distance. When the measurement module 220 detects that a desired distance has been traversed, data output module 310 generates a signal (such as an audible and/or visual signal) to the operator indicating such. Whereupon, at the second stimulation site, upon activation, a second stimulation set is generated by the programmable diagnostic device 300 and delivered to the patient via electrodes 210 and 212. The corresponding reactions are then recorded by the recording electrodes 400 and sent to the programmable diagnostic device 300. If additional stimulation sites are required, the above is repeated accordingly.

During and subsequent to the above process, the recorded data would be processed by programmable diagnostic device 300, such that data corresponding to the procedure and diagnoses would be saved and/or output to the operator in various manners.

While particular combinations of various functions and features of the present invention have been expressly described herein, other combinations of these features and functions are likewise possible. The present invention is not limited by the particular examples disclosed herein and expressly incorporates these other combinations.

The term "module" is used in the description of the various embodiments of the present invention. A module includes a processing module, a functional block, hardware, and/or software stored on memory for performing one or more functions as may be described herein. Note that, if the module is implemented via hardware, the hardware may operate independently and/or in conjunction software and/or firmware. As used herein, a module may contain one or more sub-modules, each of which may be one or more modules. As may also be used herein, the terms "processing module", "processing circuit", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

What is claimed is:
1. A system, comprising:
a diagnostic device at least operable to generate electrical stimulation signals;

an electrostimulation device having at least two electrodes, with a first of the electrodes configured as a cathode (active stimulating electrode) and a second of the electrodes configured as an anode (inactive stimulating electrode), the electrostimulation device electrically connected to the diagnostic device, the electrostimulation device operable to deliver electrical stimulation signals received from the diagnostic device to a patient via the at least two electrodes;

at least one recording electrode electrically connected to the diagnostic device, the at least one electrodes for recording indications of nerve reactions of the patient in response to the electrostimulation device delivering electrical stimulations signals to the patient; and a distance measuring device electrically connected to the diagnostic device, the distance measuring device at least configured to measure the distance between a first site on skin of the patient and a second site on the skin of the patient as the electrostimulation device is slid across the skin of the patient there between.

2. The system of claim 1, wherein the distance measuring device is integrated in the electrostimulation device.

3. The system of claim 2, wherein the diagnostic device generates a signal representing the distance the electrostimulation device has been slid across skin of the patient as measured by the distance measuring device.

4. The system of claim 3, wherein the at least two electrodes of the electrostimulation device are dry elastomer electrodes that deliver the electrical stimulation signals to the patient without the use of conductive gel positioned between the electrodes and the patient.

5. The system of claim 3, wherein the diagnostic device generates a signal when the electrostimulation device slides across the skin of the patient a predetermined distance as measured by the distance measuring device.

6. The system of claim 2, wherein the electrostimulation device includes a housing having a top and a bottom, with an aperture on the bottom to enable passage of light, from the distance measuring device, there through.

7. The system of claim 6, wherein the distance measuring device includes one or more light sources configured to emit electromagnetic energy through the aperture to an underlying surface of the skin, wherein the one or more light sources emits at least one of: visible light or infrared light.

8. The system of claim 7, wherein the distance measuring device includes a sensor assembly having an electromagnetic energy sensing module to receive at least some electromagnetic energy originating from the one or more light sources and refracted from the underlying surface to detect movement of the electrostimulation device across the skin of the patient.

9. The system of claim 2, wherein the electrostimulation device includes a housing having a top and a bottom, with an aperture on the bottom to enable passage of an infrared laser beam, from the distance measuring device, there through.

10. The system of claim 9, wherein the distance measuring device includes an illumination source for producing and directing the infrared laser beam through the aperture to an underlying surface.

11. The system of claim 10, wherein the distance measuring device includes a sensor to receive at least some refracted infrared laser beam from the underlying surface to detect the movement of the electrostimulation device across the skin of the patient.

12. A system, comprising:
an electrostimulation device having at least two electrodes, with a first of the electrodes configured as a cathode and a second of the electrodes configured as an anode, the electrostimulation device electrically connected to the diagnostic device, the electrostimulation device operable to deliver electrical stimulation signals received from the diagnostic device to a patient via the at least two electrodes;

at least one recording electrode electrically connected to the diagnostic device, the at least one electrodes for recording indications of nerve reactions of the patient in response to the electrostimulation device delivering electrical stimulations signals to the patient; and a distance measuring device electrically connected to the diagnostic device, the distance measuring device at least configured to measure a distance between a first site on skin of the patient and a second site on the skin of the patient when the electrostimulation device is moved over the skin there between.

13. The system of claim 12, wherein at least a portion of the distance measuring device is integrated in the electrostimulation device.

14. The system of claim 13, and further including a signal generator that generates a signal representing the distance the electrostimulation device has been moved over the skin of the patient as measured by the distance measuring device.

15. The system of claim 14, wherein the at least two electrodes of the electrostimulation device are dry elastomer electrodes that deliver the electrical stimulation signals to the patient without use of conductive gel positioned between the electrodes and the patient.

16. The system of claim 15, wherein the signal generator generates a signal when the electrostimulation device has been moved a predetermined distance over the skin of the patient as measured by the distance measuring device.

* * * * *